US006231621B1

United States Patent
Sørensen et al.

(10) Patent No.: US 6,231,621 B1
(45) Date of Patent: May 15, 2001

(54) DIAMINOBENZOIC ACID DERIVATIVES AS DYE PRECURSORS

(75) Inventors: Niels Henrik Sørensen, Skævinge; Ole Kirk, Virum; Rikke Lolck, Smørum; Torben Desler, Copenhagen, all of (DK)

(73) Assignee: Novozymes A/S, Bagsuaerd (DK)

( * ) Notice: Subject to any disclaimer, the term of this patent is extended or adjusted under 35 U.S.C. 154(b) by 0 days.

(21) Appl. No.: 09/271,540

(22) Filed: Mar. 18, 1999

Related U.S. Application Data

(63) Continuation of application No. PCT/DK97/00435, filed on Oct. 8, 1997.

(30) Foreign Application Priority Data

Oct. 8, 1996 (DK) .................................................. 1104/96

(51) Int. Cl.[7] .................................................. A61K 7/13
(52) U.S. Cl. .................................................. 8/401; 8/416
(58) Field of Search ................. 8/401, 411, 416, 8/649; 564/305

(56) References Cited

U.S. PATENT DOCUMENTS

| 3,251,742 | | 5/1966 | Soloway ................................. 167/88 |
| 3,893,803 | * | 7/1975 | Kaiser ................................. 8/401 |
| 3,957,424 | * | 5/1976 | Zeffren et al. ................................. 8/401 |
| 5,380,719 | * | 1/1995 | Kim ................................. 514/85 |
| 5,972,042 | * | 10/1999 | Barfoed et al. ................................. 8/401 |
| 6,004,355 | * | 12/1999 | Dias et al. ................................. 8/401 |
| 6,022,381 | * | 2/2000 | Dias et al. ................................. 8/401 |
| 6,063,729 | * | 3/2000 | Barfoed et al. ................................. 8/401 |

FOREIGN PATENT DOCUMENTS

| 291 094 A5 | 6/1991 | (DE) . |
| 504 005 A1 | 9/1992 | (EP) . |
| WO 97/19999 | 6/1997 | (WO) . |
| WO 97/37633 | 10/1997 | (WO) . |

* cited by examiner

Primary Examiner—Caroline D. Liott
(74) Attorney, Agent, or Firm—Elias J. Lambiris, Esq.

(57) ABSTRACT

The invention relates to substrates which develops color on oxidation of general formula (I). The invention also relates to the use of said substrates for dyeing, e.g. keratinous fibers, in particular hair, dyeing textiles, a dyeing composition and a method for dyeing keratinous fibers.

8 Claims, 11 Drawing Sheets

Theoretic curve

Figure 1:
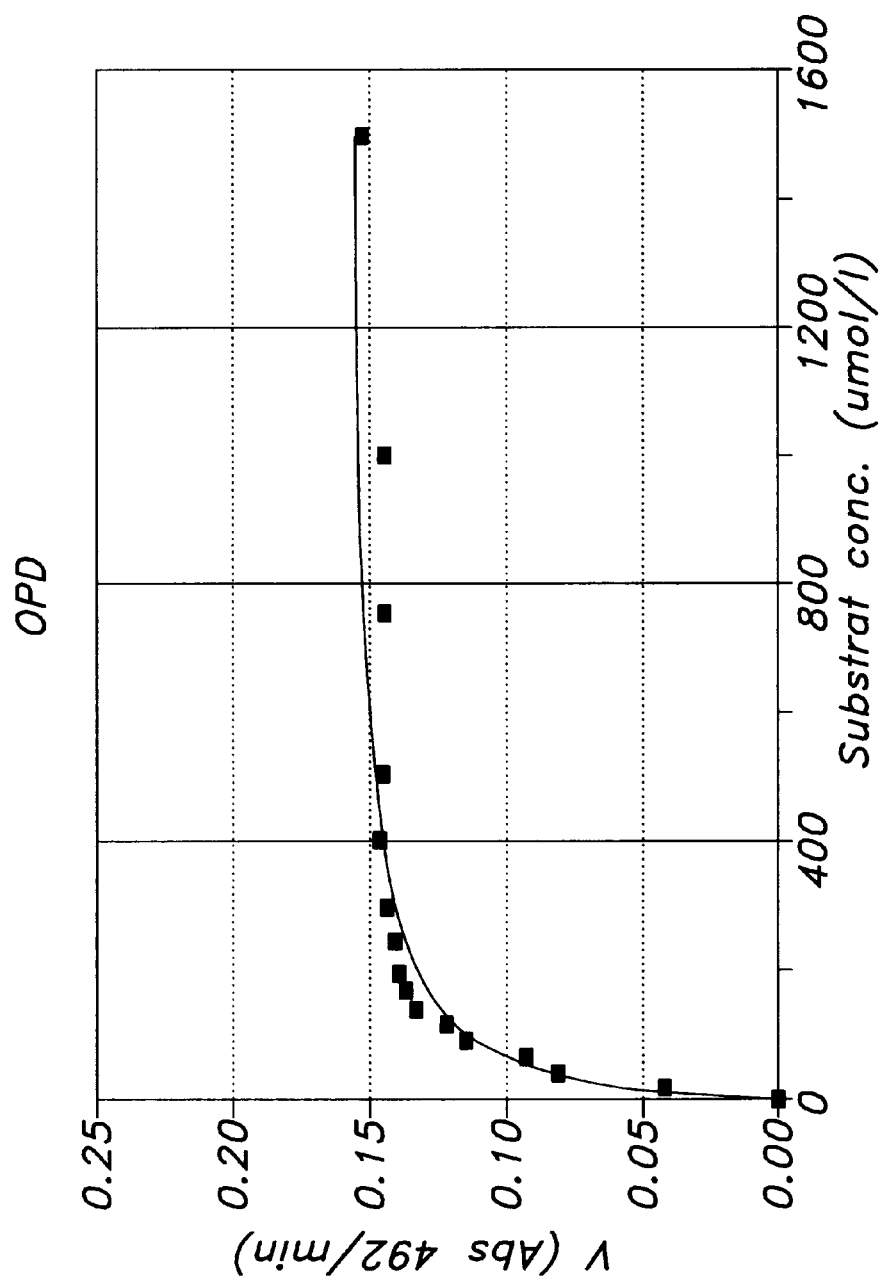

1 Ethylester 2 Isopropylester 3 Methylester 4 DABA 5 OPD

DIAMINOBENZOIC ACID DERIVATIVES AS DYE PRECURSORS

CROSS-REFERENCE TO RELATED APPLICATIONS

This application is a continuation of PCT/DK97/00435 filed Oct. 8, 1997 and claims priority under 35 U.S.C. 119 of Danish application 1104/96 filed Oct. 8, 1996, the contents of which are fully incorporated herein by reference.

FIELD OF THE INVENTION

The present invention concerns the use of aminobenzoic acid (DABA) as a substitute for e.g. o-phenylendiamine (OPD) in analyses based on peroxidases as well as a dyeing substrate (i.e. a dye precursor) in dyeing compositions, and as an substrate for dyeing natural and synthetic fibres including textiles, thread and yarns. The invention also relates to a composition adapted for dyeing keratinous fibres, e.g. hair, wool, fur and hides, and a method for dyeing such keratinous fibres.

BACKGROUND OF THE INVENTION

Immuno-chemical Assays

Several different substrates are known in the part to be used for enzyme systems in connection with peroxidase-based immuno-chemical assays, for example ELISA. These substrates are often toxic, mutagenic or carcinogenic.

ELISA (Enzyme Linked Immuno Sorbent Assay) is a method used to assess the amount of antibody in serum. The main principle is that in a much diluted solution many antigens will become bound to the surface of plastic. Thus, if a much diluted solution of antigens is incubated for a time in plastic trays it is possible to wash the cavities in a buffer solution and still retain the film of antigens on the surface of the plastic. If it is required to determine the amount of antibodies in, for instance, serum then the trays with their deposits of antigens are incubated with the serum, The antibodies attach themselves to the antigens and, after thorough washing the trays are again incubated this time with a marker, for example anti-immune globulin serum to which there is attached a suitable enzyme by covalent bonding. In this particular case peroxidase is used.

The peroxidase-marker complex will attach itself to those locations where there is already a deposit of antibodies. After thorough washing to remove all un-combined material the enzyme activity is measured, normally by the use of a suitable colour indicator. Enzyme activity may be determined by the addition of a cromogenetic substrate (i.e. colour producing compound) and hydrogen peroxide. The enzyme catalyses the reduction of the substrate to a coloured compound and the resultant degree of absorbency provides a measure of the enzyme activity. If the serum contains no antibodies there will be no enzyme activity, on the other hand if there is much antibody present there will be very considerable enzyme activity. A standard curve can be drawn showing enzyme activity as a function of the concentration of antibodies. This may be used to estimate the content of antibodies in unknown serum samples by interpolation.

Many of the peroxidase substrates are aromatic amines and include diaminobenziden (DAB), 3,3'-diamino benzid tetra hydrochloride, 3,3',5,5'-tetra methyl benzidin (TMD). Another peroxidase substrate, which does not belong to the group of aromatic amines, is 2,2-azino-di (3-ethyl-benzo thiazolin-6-sulphonic acid) (AEBTS), this has been used as a standard for the establishment of the activity of peroxidase preparations. According to Voogd, Van der Stel and Jacobs (1980) this material is also a mutagent.

o-phenylendiamine (OPD) is another peroxidase substrate which is widely used in hospital and development laboratories. OPD is known to be both mutagenic and carcinogenic.

The staff of laboratories in which analyses involving the use of toxic, mutagenic or carcinogenic materials are carried out are exposed to a significant degree of risk of coming into direct contact with these materials. In order to provide a safe working environment considerable efforts are now made to substitute these dangerous materials with less dangerous ones.

Hair Dyeing Composition

In addition to being used as a substrate in immuno-chemical assays OPD is used to dye hair. In this connection too it is desirable to substitute a dangerous material with one less dangerous so that the user is not exposed to danger by coming into contact with it. To protect the hands against the dangerous material it is normal for gloves to be used while the hair dye is being applied. Gloves cannot, of course, protect the scalp of the person to whom the dye is applied.

In general hair dyeing compositions on the market today can be divided into three main groups:

temporary hair dyes,
semi-permanent hair dyes, and
permanent oxidative hair dyes.

The temporary hair dyes are only intended to change the natural hair colour for a short period of time and usually functions by depositing dyes on the surface of the hair. Such hair dyes are easy to remove with normal shampooing.

When using semi-permanent hair dyes the colour of the dyed hair can survive for five or more shampooings. This is achieved by using dyes having a high affinity for hair keratin and which is able penetrate into the interior of the hair shaft.

Permanent hair dyes are very durable to sunlight, shampooing and other hair treatments and need only to be refreshed once a month as new hair grows out. with these dyeing systems the dyes are created directly in and on the hair. Small aromatic colourless dye precursors (e.g. p-phenylene-diamine, o-aminophenol, o-phenylendiamine (OPD)) penetrate deep into the hair where said dye precursors are oxidised by an oxidising agent into coloured polymeric compounds. These coloured compounds are larger than the dye precursors and can not be washed out of the hair.

By including compounds referred to as modifiers (or couplers) in the hair dyeing composition a number of hair colour tints can be obtained. Cathecol and Resorcinol are examples of such modifiers.

Some of the today most widely used dye precursors such as OPD are known to be both mutagenic and carcinogenic.

Further, traditionally $H_2O_2$ is used as the oxidizing agent (colour builder), but also as a bleaching agent. Dyeing compositions comprising $H_2O_2$ are often referred to as "lightening dyes" due to this lightening effect of $H_2O_2$.

The use of $H_2O_2$ in dyeing compositions have some disadvantages as $H_2O_2$ damages the hair. Further, oxidative dyeing often demands high pH (normally around pH 9–10), which also inflicts damage on the hair and on the skin. Consequently, if using dye compositions comprising $H_2O_2$ it is not recommendable to dye the hair often.

To overcome the disadvantages of using $H_2O_2$ it has been suggested to use oxidation enzymes to replace $H_2O_2$.

U.S. Pat. No. 3,251,742 (Revlon) describes a method for dyeing human hair by dye formation in situ (i.e. on the hair). An oxidation enzyme is used for the colour formation reactions at a substantially neutral pH (7–8.5). Laccases, tyrosinases, polyphenolases and catacolases are mentioned as suitable oxidation enzymes. The hair colour pigment is formed by controlled oxidation of various quinone-forming compounds and mono or poly aromatic amines having the amino groups on the aromatic rings to form natural appearing pigments. Specifically mentioned dye precursors are 2-amino-4-nitrophenol, p-phenylene diamine, m-phenylene diamine, o-phenylene diamine, 2-amino-1,4-naphthoquenone, m-aminophenol, p-aminophenol, o-aminophenol, 2-amino resorcinol, 1,2,4-benzene triamine, nitro-p-phenylene diamine, 2-amino-5-diethyl amino toluene.

EP patent no. 504.005 (Perma S. A.) concerns dyeing compositions for keratinous fibres, in particular hair, which do not require the presence of $H_2O_2$ (hydrogen peroxide). The composition comprises an enzyme capable of catalysing the formation of the polymeric dyes and also dye precursors, such as bases and couplers, in a buffer solution wherein the pH of said composition is between 6.5 and 8 and said enzyme has an optimal activity in the pH range between 6.5 and 8. *Rhizoctonia praticola laccase* and *Rhus vernicifera laccase* are exemplified as the oxidation enzyme to oxidize the dye precursor(s). The following dye precursors are specifically mentioned: p-phenylene diamine, o-aminophenol, p-methylaminophenol, p-aminophenol, p-toluylenediamine and N-phenyl-p-phenylene diamine.

The aim of the present invention is to use the present findings to make available a substrate which to all intents and purposes is non-toxic, non-mutagenic and/or non-carcinogenic and which may be used in immuno-chemical assays, for the dying of keratinous fibres, in particular hair and for dying both natural and synthetic fibres, e.g. textiles. This aim is achieved by utilising the discovery of a substrate which includes the group with the general formulae shown in 1.

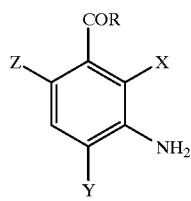

(I)

wherein
R is an amino, mono- or a distributed amino or OR', where R is H, alkyl, alkenyl, alkynyl, halogenalkyl, nitro, benzyl, phenyl or substituted phenyl. X, Y and Z may each be any one of the following: alkyl, alkenyl, alkynyl, halogenalkyl, nitro, benzyl, phenyl, substituted phenyl, amino, hydroxy or mercapto with the proviso that at least one of the groups X, Y and Z is an amino group or an amino salt.

In a special embodiment of the invention a substrate is made available which includes a connection with formula 1 where R' is a methyl, ethyl or iso propyl group.

In an preferred embodiment the substrate is a benzoic acid ester, in particular 3,4-diaminobenzoic acid methyl ester (DABA-Me), 3,4-diaminibenzole acid ethyl ester and 3,4-diamino benzoic acid isopropyl ester.

Comparison of the very toxic aniline with the carboxyl acid derivative of aniline, p-amino benzoic acid (PABA) shows that the toxic city of the molecule is radically altered by the addition of the carboxyl group. PABA is generally considered to be non-toxic and, among other applications, is used as an ultra violet filter in sun lotions. If the substrate OPD is thought of along the same lines it can be seen that a possible analogue is 3,4-diamino benzoic acid (3,4-DABA) n This material is comparatively cheap and readily obtainable.

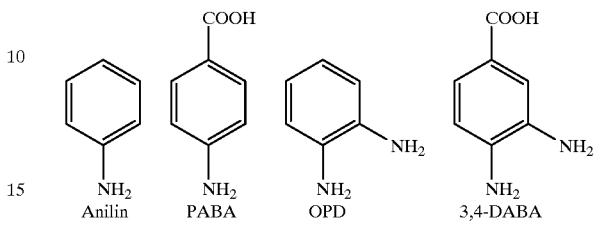

Anilin    PABA    OPD    3,4-DABA

Investigation using enzymes showed that 3,4-DABA is a considerably poorer substrate for peroxidase than is OPD. In other words 3,4-DABA has a higher $K_m$-value at the same $V_{max}$ when compared with OPD. This is apparently due to the carboxyl group's inductive (deactivating) effect upon the aromatic ring. This effect can be countered by modifying the carboxyl group, for example by esterification with an alcohol. The preferred alcohols are methanol, ethanol and iso propcanol. Methyl, ethyl and isopropyl esters were examined in connection with enzymes and the materials were shown to have significantly improved properties than 3,4-DABA. Especially the ethyl ester was found to have a very high $V_{max}$, i.e. at the same concentration it gives a very much higher reaction speed than OPD.

The reaction mechanism for the oxidation of OPD with, for instance, hydrogen peroxide, both with and without an enzyme, is described by the following equations:

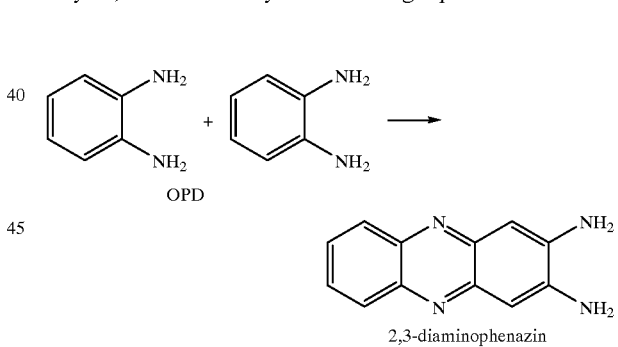

OPD 2,3-diaminophenazin

It may be seen from this that the product of oxidation is 2,3-diamino phenazin.

When one of the compounds described here is employed the product of oxidation is also an amino phenazine. In the case of 3,4-DABA the oxidation product is 4,7-dicarboxy-1,2-diamino phenazine as shown in the following equation.

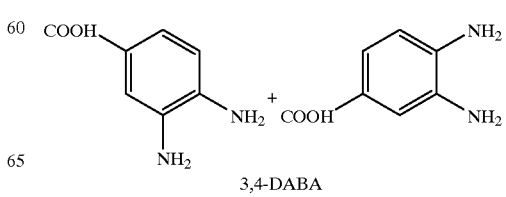

3,4-DABA

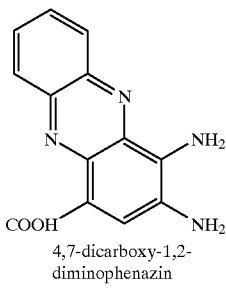
4,7-dicarboxy-1,2-diminophenazin

The substrate should have two amino groups at the 3,4-location for the reaction to take place. However, substrates which have the amino groups at either the 2,3-location or the 3,4-location may be used but only if the carboxyl group does not hinder the reaction.

Substrates which have the amino group at the para location may also be used to produce a coloured product. An example of this is 3,6-DABA.

In order to counteract the carboxyl groups inductive effect (i.e. deactivation of the aromatic ring caused by the groups attractive effect upon electrons) esterification of the carboxyl group was investigated using electron donating groups to see if deactivation could be counteracted while at the same time retaining non-mutagenic attributes. To investigate the effect of different alkyl groups on the material's enzymatic properties as well as possible mutagenic properties the methyl, ethyl and isopropyl esters of 3,4-DABA were synthesised.

Compounds with the general formulae 1 are preferably dissolved in DMF (Dimethyl formamide) but other organic solvents may be used for this purpose. If a compound with the general formulae 1 is in the form of a salt it can be dissolved in water and this is preferred when using organic solvents.

In another aspect the invention relates to a method for quantitative and/or qualitative analysis of a material of biological interest. In this case a peroxidase enzyme together with a marker is bound to the compound in question. Hydrogen peroxide is then converted with a cromogenetic substrate (i.e. colour forming compound) in the presence of the peroxidase, the substrate includes a bond with the general formulae 1.

In a preferred embodiment of the method of the invention one of the following substrates are used: the methyl, propyl or isopropyl ester of amino benzoic acid.

In those cases where the material of biological interest is an antigen the associated antibody is used. In this connection other combinations will suggest themselves to the skilled person.

The coloured product produced by the method of the invention is especially suited to the dying of textiles, thread, yarn, wool, hides and skins and human hair. Other natural fibres such as cotton and silk may also be dyed with the product as may synthetic fibres such as polyamides, polyurethane and polyester.

The coloured product may either be made immediately before it is to be used for dying or it may be synthesised in the immediate vicinity of the substance to be dyed. For example this may be done by mixing the substrate and the oxidation system in a person's hair.

The dyeing process may be carried out rinsing the person's hair with a mixture of the substrate of the invention and hydrogen peroxide or an oxidation enzyme. A peroxidase is then added and distributed in the hair. When the desired degree of colouring has been obtained the hair is rinsed with water.

The substrate may be mixed with the oxidation system before it is applied to the hair. As stated above the substrate may be oxidised with hydrogen peroxide or an oxidation enzyme generating hydrogen peroxidase in the presence of a peroxidase.

Peroxidases belongs to the group of enzymes which is known as the oxidoreductases. The group also includes the classes of enzymes dehydrogenase, oxygenase, oxidase, laccase and related enzymes. These enzymes may also be used for as an oxidation system/agent for e.g. dyeing keratinous fibres, such as hair, wool, fur and hides and the like. Dyeing composition and preferred oxidation enzymes will be described further below.

In oxidation reactions which are catalysed by the enzyme peroxidase the oxygen donor is hydrogen peroxide which is used as an electron acceptor. Oxidases employ oxygen as an electron acceptor.

Examples of suitable oxidases include catecholoxidase, laccase and o-amino phenoloxidase.

Oxidation systems which may be used for the oxidation of the substrate in this connection therefore include peroxidase and hydrogen peroxide as well as oxidases, laccases and related enzymes and oxygen. When the system consists of only an oxidase and oxygen it is only necessary to add the oxidase to the substrate as the oxygen in the air is used as an oxidant.

Dyeing Composition

In an aspect the invention relates to a composition in particular adapted for dyeing keratinous fibres comprises, e.g. hair, fur, hide or wool. Comprising 1) at least one oxidation enzyme 2) at least one substrate as defined by the formulae 1 and optionally 3) at least one modifier.

A preferred use of the composition is as a permanent dye for the dyeing of human hair.

The oxidation enzyme is as also indicated above an oxidoreductase, i.e. an enzyme classified under the Enzyme Classification number E.C. 1 (Oxidoreductases) in accordance with the Recommendations (1992) of the International Union of Biochemistry and Molecular Biology (IUBMB)) which catalyses oxidoreduction reactions.

Within the class of oxidoreductase enzymes are preferred enzymes which catalyse the oxidation of a substrate (an electron or hydrogen donor) by acting on oxygen ($O_2$) and/or a peroxide as the acceptor. Such enzymes include enzymes classified within the enzyme classes comprising oxidases, including E.C. 1.1.3. E.C. 1.2.3, E.C. 1.3.3, E.C. 1.4.3, E.C. 1.5.3, E.C. 1.7.3, E.C. 1.8.3 and E.C. 1.9.3, laccases and related enzymes in E.C. 1.10.3, and peroxidases in E.C. 1.11.

According to the invention three types of oxidoreductases are specifically contemplated:
  a) Laccases or related enzymes, which act on molecular oxygen and yield water ($H_2O$) without any need for peroxide (e.g. $H_2O_2$),
  b) Oxidases, which act on molecular oxygen ($O_2$) and yield peroxide ($H_22O$), and
  c) Peroxidases, which act on peroxide (e.g. $H_2O_2$) and yield water ($H_2O$)

Also, enzyme systems which comprise a combination of more than one enzyme from a single class or from different classes among the three types of enzymes are contemplated. In the present specification, although reference will often be made to a single enzyme for the sake of simplicity, it is to be understood that the description is generally applicable to such combinations of more than one enzyme. Further, although the invention is generally described in terms of the preferred aspect relating to the dyeing of hair, it is to be understood that the description is generally applicable to compositions according to the invention adapted for dyeing of other types of keratinous fibres.

Particularly preferred enzymes are laccases and related enzymes, the term "laccases and related enzymes" including enzymes comprised by the enzyme classification E.C. 1.10.3.2 (laccases) and catechol oxidase enzymes comprised by E.C. 1.10.3.1, bilirubin oxidase enzymes comprised by the enzyme classification E.C. 1.3.3.5 and mono-phenol mono-oxygenase enzymes comprised by the enzyme classification E.C. 1.14.99.1. Laccases are multi-copper containing enzymes that catalyze the oxidation of phenols and aromatic amines. Laccase-mediated oxidation results in the production of aryloxy-radical intermediates from suitable phenolic substrates; the ultimate coupling of the intermediates so produced provides a combination of dimeric, oligomeric, and polymeric reaction products. Certain reaction products can be used to form dyes suitable for dyeing hair.

Preferably, the laccase employed may be derived from a strain of Polyporus sp., in particular a strain of *P. pinsitus* or *P. versicolor*, a strain of Myceliophthora sp., e.g. *M. thermophila*, a strain of Rhizoctonia sp., in particular a strain of *Rh. praticola* or *Rh. solani*, a strain of a Rhus sp., in particular *Rhus vernicifera*, a strain of Pyricularia sp, in particular *P. oryzae*, or a strain of Scytalidium, such as *S. thermophilium*.

In specific embodiments of the invention the oxidoreductase is a laccase such as a Polyporus sp. laccase, especially the *Polyporus pinisitus* laccase (also called *Trametes villosa* laccase) described in WO 96/00290 (from Novo Nordisk Biotec Inc.) or a Myceliophthora sp. laccase, especially the *Myceliophthora thermophila* laccase described in WO 95/33836 (from Novo Nordisk Biotech Inc.).

Further, the laccase may be a Scytalidium sp. laccase such as the *S. thermophilium* laccase described in WO 95/33837 and WO 97/19998 (from Novo Nordisk Biotech Inc.), the contents of which is incorporated herein by reference, or a Pyricularia sp. laccase, such as the *Pyricularia oryzae* laccase which can be purchased from SIGMA under the trade name SIGMA No. L5510, or a Coprinus sp. laccase, such as a *C. cinereus* laccase, especially a *C. cinereus* IFO 30116 laccase, or a Rhizoctonia sp. laccase, such as a *Rh. solani* laccase, especially the neutral *Rh. solani* laccase described WO 95/07988 (from Novo Nordisk A/S) having a pH optimum in the range from 6.0 to 8.5.

The laccase may also be derived from a fungus such as Collybia, Fomes, Lentinus, Pleurotus, Aspergillus, Neurospora, Podospora, Phlebia, e.g. *P. radiata* (WO 92/01046), Coriolus sp., e.g. *C. hirsitus* (JP 2-238885), or Botrytis.

Bilirubin oxidase may preferably be derived from a strain of Myrothecium sp., such as *M. verrucaria*.

The substrates (i.e. dye precursors) may according to the dyeing composition of the invention be any of the above within the definition of the general formulae 1.

Preferred dye precursors (i.e. substrates) are benzoic acid esters, especially diamino benzoic acid esters, in particular 3,4-diamino benzoic acid methyl ester (DABA-Me), 3,4-diamino benzoic acid ethyl ester and 3,4-diamino benzoic acid isopropyl ester.

Other Oxidation Agents

The substrate may also be oxidised by a number of inorganic compounds, among these are compounds which include hypochlorite ($ClO^-$), hypobromite ($BrO^-$), permanganate ($MnO_4^-$) dicromate ($Cr_2O_7^{2-}$) and the iron ion ($Fe^{3+}$).

Oxidation systems are taken to be either an oxidant per se or a combination of an enzyme and an oxidant.

Modifiers

Modifiers typically incorporation in a dye compositions include m-aromatic diamines, m-aminophenols, polyphenols, amino naphthalines or naphthols. The modifier (coupler) reacts with the dye precursor in the presence of the oxidative enzyme or the like, converting it into a coloured compound. Examples of specific modifiers (couplers) include m-phenylene-diamine, 2,4-diaminoanisole, 1-hydroxynaphthalene (α-naphthol), 1,4-dihydroxybenzene (hydroquinone), 1,5-dihydroxynapthalene, 1,2-dihydroxybenzene(pyrocatechol), 1,3-dihydroxybenzene (resorcinol), 1,3-dihydroxy-2-methylbenzene, 1,3-dihydroxy-4-chlorobenzene (4-chlororesorcinol), 1,2,3, trihydroxybenzene, 1,2,4-trihydroxybenzene, 1,2,4-trihydroxy-5-methylbenzene, and 1,2,4-trihydroxytoluene.

Method of Dyeing Keratinous Fibres

In a further aspect the invention relates to a method for dyeing keratinous fibres, in particular hair, fur, hide and wool, using a composition as described above. The dyeing method can be conducted with one or more dye precursors (i.e. substrates of the invention) and optionally in combination with one or more modifiers. The amount of dye precursor(s) and other ingredients used in the composition of the invention for this purpose are in accordance with usual commercial amounts and therefore known for the skilled person. Hair dyeing is typically carried out at or near room temperature, preferably around the optimum temperature of the enzyme being used, and at a pH in the range of from 3.0 to 9.0, preferably 4.0 to 8.5, especially 6.0 to 8.0. Dye precursors (i.e. substrates of the invention) and optional modifiers are described above.

The invention is further illustrated in the following non-limiting example.

EXAMPLE 1

Synthesis of 3,4-diamino Benzoic Acid Esters

The esters were made starting from 4-amino-3-nitrotoluene, followed by the esterification and reduction of 4-amino-3-nitrobenzoicacid esters to 3,4-diamino benzoic acidester. The reactions are shown below.

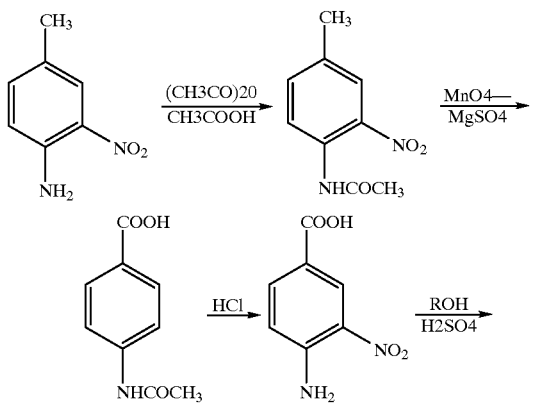

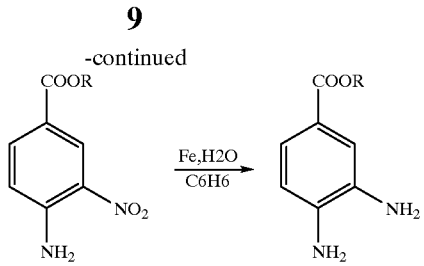

Preparation of Esters of 3,4-DABA

The amino group in 4-amino-3-nitrotoluene is protected by boiling in anhydrous acetic acid in acetic acid. The methyl group is oxidized with permanganate in an aqueous solution containing magnesium sulphate. the acetyl group is removed by boiling with 0.1 hydrochloric acid. After isolation and drying 4-amino-3-nitrobenzoicacid is dissolved in absolute alcohol and concentrated sulphuric acid is added. On boiling for two to five hours the acid groups are esterified. The exact boiling time depends on the type of alcohol. The last stage is the reduction of the isolated product with activated iron and water in boiling benzine for about five hours.

When the reaction was complete the iron particles were filtered out and the residue dried for between 24 to 48 hours over anhydrous sodium sulphate. After filtration and evaporation the ester was recrystallised in a mixture of n-butanol and benzine in the ratio of 1 to 10.

The above procedure was used to produce 3,4-DABA esters for measurement of enzymes and for mutagenetic testing. If larger amounts were to be required at a reasonable price then direct esterification of 3,4-DABA would be preferred. Thus the methyl ester may be prepared by bubbling hydrochloric acid gas through a solution of 3,4-DABA containing methanol. This last method finds only limited use in the production of the ethyl ester and cannot be used to produce the isopropyl ester.

Characterization of 3,4-DABA Esters

Thin layer chromatography.

The DABA esters that were prepared were analysed and compared with the help of thin layer chromatography (TLC) using silica gel plates of the type MERC 60 $F_{254}$ the stock number of the zone of concentration was 5583. A mixture of chloroform, methanol and acetic acid in the ratio of 90:5:5 on a volumetric basis was used as a solvent For the purpose of comparison OPD and 3,4-DABA were analyzed on the same plate. The Rf values obtained are shown in Table 1.

TABLE 1

| Chemical bond | Rf - value |
| --- | --- |
| 3,4-DABA | 0.15 |
| OPD | 0.19 |
| Methyl ester | 0.29 |
| Ethyl ester | 0.31 |
| Isopropyl ester | 0.33 |

It can be seen from table 1 that the bigger alkyl groups give a measurably greater displacement in the solvent which contains chloroform. The least displacement is seen, as might be expected, with 3,4-DABA which contains a free carboxyl group. All the combinations tested moved in the form of patches which is an indication of their purity.

The fact that the 3,4-DABA esters are lipeds gives no problems with regard to solubility in water when making up solutions of substrates. A standard solution of dimethyl formamide diluted in an aqueous buffer with a pH of 5.0. At high concentrations of substrate oxidation products formed by the action of enzymes may cause slight turbidity in the solution. By reducing the pH to about 1 with 1M sulphuric acid a completely clear solution is produced. This is due to the addition of protons to the amino groups.

Determination of Melting Points

To verify that the materials synthesised were identical with those described in the literature their melting points were determined and compared with values given in a table on page 1532 of Chapman and Hall's Dictionary of Organic Compounds, Fifth Edition, Volume 2. Melting points were determined by the use of the capillary tube method using a silicone oil bath.

Melting points are given in Table 2.

TABLE 2

| Material literature | Measured melting point | Value from |
| --- | --- | --- |
| methyl ester | 108–109° C. | 108–109° C. |
| ethyl ester | 112–113° C. | 112–113° C. |
| isopropyl ester | 73–74° C. | — |

It can be seen from the above table that there is close agreement between the melting points determined by experiment and the melting points as given in the literature. It may, therefore, reasonably be assumed that the synthesised material are identical with those described in the literature. It was not possible to find a value for the isopropyl ester in the literature.

Ultraviolet Spectroscopy.

UV spectra were taken of OPD as well as the methyl, ethyl and isopropyl esters.

Scanning was done from 360 nm to 210 nm using a solution of the compounds in methanol. The concentration was 0.1/l. Table 3 shows the absorption maxima and the extinction coefficients for the compounds investigated.

TABLE 3

| Material | Absorption max. | Extinction coefficient |
| --- | --- | --- |
| OPD | 290.0 nm | 2000 $M^{-1}$ |
|  | 231.3 nm | 3400 $M^{-1}$ |
| methyl ester | 310.0 nm | 6000 $M^{-1}$ |
|  | 277.5 nm | 6000 $M^{-1}$ |
|  | 232.5 nm | 8400 $M^{-1}$ |
| ethyl ester | 310.0 nm | 6200 $M^{-1}$ |
|  | 277.5 nm | 6000 $M^{-1}$ |
|  | 232.5 nm | 8600 $M^{-1}$ |
| isopropyl ester | 310.0 nm | 6500 $M^{-1}$ |
|  | 277.5 nm | 6200 $M^{-1}$ |
|  | 232.5 nm | 8700 $M^{-1}$ |

As can be seen from the above table all three esters absorb at the same wavelength. At 237.5 nm there is a slight increase in extinction with increasing molecular weight of the alkyl group. 3,4-DABAA-esters show a typical maximum at 277.5 nm. This maximum is not found in OPD because of the ester carbonyl group.

In order to investigate the properties of 3,4-DABA and the three esters with respect to oxidation catalyzed by peroxidase a series of measurements were carried out on the enzymatic reactions initial velocity with increasing concentration of the substrate. Measurements were carried out on OPD,3,4-DABA, 3,4-DABA-methyl ester, 3,4-DABA-ethyl ester, and 3,4-DABA isopropyl ester.

Absorbancy at 492 nm was used as a measure of the course of the reaction. The initial velocity was taken to be the absorbancy at 492 nm two minutes after the addition of the peroxidase to a mixture of the substrate and hydrogen peroxide in a buffer with a pH of 5.0. The wavelength of 492 nm was chosen because it is employed in the standard assay procedures for OPD. None of the substrates has a specially high absorption at this wavelength.

By varying the concentration of the substrate and at the same time measuring the initial velocity of the reaction it is posible to apply the Michaelis/Menten equation tothe system.

Under ideal conditions the values determined experimentally will approach the value of the expression:

$$V_{init} = \frac{V_{max}}{1 + \frac{K_m}{[S]}}$$

where [S] is the concentration of the substrate, $V_{max}$ is the maximum initial concentration which is reached in the particular assay. $K_m$ is defined as the concentration of the substrate at $V_{max}/2$. A small $K_m$ value will therefore be characteristic for an enzyme system where a low concentration of the substrates produces saturation of the enzyme.

The expression im plies that the initial velocity will increase with increasing concentration of the substrate, but the curve for the velocity will flatten out and approach $V_{max}$ for very high concentrations of the substrate. In actual fact the parameter $K_{kat}$ be calculated as $V_{max}/[E]$ where [E] is the molar concentration of the enzyme in the reaction. $K_{kat}$ is the same as $min^{-1}$ and reflects the activity of the enzyme in a saturated solution upon the substrate.

The peroxidase system has an extremely complicated energy balance (Arnoa et al. (1990)) for short periods of less than a minute the system may nevertheless be described in terms of the above given formulae.

EXAMPLE 2
Enzymatic Determination

The following solutions were prepared for use in the enzyme assay:

a) Assay buffer:

A 50 mM phosphate/citrate buffer with a pH of 5.0 was made by mixing a 50 mm $Na_2 HPO_4$ solution and a 50 mm solution of citric acid. The pH was measured while mixing was in progress.

b) DMF diluted 1:10:

By means of pipette 10 ml were placed in a graduated flask which was then topped up to 100 ml with assay buffer.

c) Solution of hydrogen peroxide 0.018%: 15 µl of a 30% solution of hydrogen peroxide (PERHYDROL, Merck) was thinned down with 25 ml of the assay buffer.

d) Stabilizing buffer for peroxidase:

The stabilizing buffer for peroxidase, i.e. a buffer which stabilizes the enzyme, was prepared according to the method of Olsen and Little (1983). A 0.1M Na-acetate buffer, which was 0.5M in terms of $CaCl_2$ was adjusted to pH 5.6.

37.5 mg N-acetyl-trimethyl-ammonium-bromide was dissolved in 75 ml of the buffer. To this solution 25 ml of glycerol was added. The enzyme activity is maintained in this buffer because the molecules of the enzyme are prevented from aggregating.

e) Standard solution of peroxidase:

10 mg of horseradish peroxidase type VI-A (Sigma no. 6782) were dissolved in 10 ml of the stabilizing buffer. This was stored at −15° C. This will keep for several months (Olsen and Little (1983)).

f) Bench solution of peroxidase:

The standard peroxidase solution was diluted to 1:1000 with the 10 ml assay-buffer solution in 10 µl standard solution.

g) Standard solutions of the substrates:

0.5 mmol of each substrate in 5 ml DMF. These solutions will keep for several weeks at −15° C.

h) Bench solutions of the substrates.

The standard solutions were diluted by 1:10 with the assay buffer. Before being used the substrate solutions were diluted by 1:10. 0.5 ml of the standard solution was thinned down with 4.5 ml of the assay buffer Measurement of the Velocity of Reaction as a Function of the Concentration of the Substrates For each of the compounds OPD, 3,4-DABA-, and the methyl, ethyl, and isopropyl esters of 3,4-DABA 15 measurements were carried out and absorbency was measured twice in each case at 492 nm one minute after the addition of 100 µl dilute peroxidase solution (bench solution). The concentration of the peroxidase was held constant at 50 ng/ml during the whole investigation. By using the volume of substrate and the volumes of 10 vol-% DMF solution as given in table 4 it was possible to employ a constant reaction volume and a constant concentration of DMF. For all measurements there was used 1550 µl buffer and 50 µl bench solution of peroxidase. The total volume is then as follows: 300 µl DMF and substrate solution, 1550 µl buffer, 100 µl bench solution of peroxidase and 50 µl hydrogen peroxide solution. That is 2000 µl in total.

TABLE 4

| µl substrate solution | µl 10% DMF-solution | Substrate concentration (µmol/l) |
|---|---|---|
| 0 | 300 | 0 |
| 5 | 295 | 25 |
| 10 | 290 | 50 |
| 15 | 285 | 75 |
| 20 | 280 | 100 |
| 25 | 275 | 125 |
| 30 | 270 | 150 |
| 35 | 265 | 175 |
| 40 | 260 | 200 |
| 50 | 250 | 250 |
| 60 | 240 | 300 |
| 80 | 220 | 400 |
| 100 | 200 | 500 |
| 150 | 150 | 750 |
| 200 | 100 | 1000 |
| 300 | 0 | 1500 |

Table 5 contains information about the values measured for $K_m$, $V_{max}$ and $K_{kat}$ for the five compounds.

TABLE 5

| Substrate | $K_m$ (µmol/µl) | $V_{max}$ (min$^{-1}$) | $K_{kat}$ (1 * mol$^{-1}$ 1 * min$^{-1}$) |
|---|---|---|---|
| OPD | 47.35 | 0.16 | 1.6 * 10$^8$ |
| 3,4-DABA | 251.22 | 0.20 | 2.0 * 10$^8$ |
| methyl ester | 125.97 | 0.22 | 2.2 * 10$^8$ |
| ethyl ester | 212.39 | 0.27 | 2.7 * 10$^8$ |
| isopropyl ester | 118.46 | 0.22 | 2.2 * 10$^8$ |

The results of the measurements of initial velocities are stated in units of absorbency and not in molar units. In order to be able to measure the "true" velocity of reaction it is necessary to isolate the oxidation product for each substrate and determine the molar extinction coefficient. The value of Kkat is worked out from 1 mole of peroxidase of 50,000 g/mol.

Figure 2:
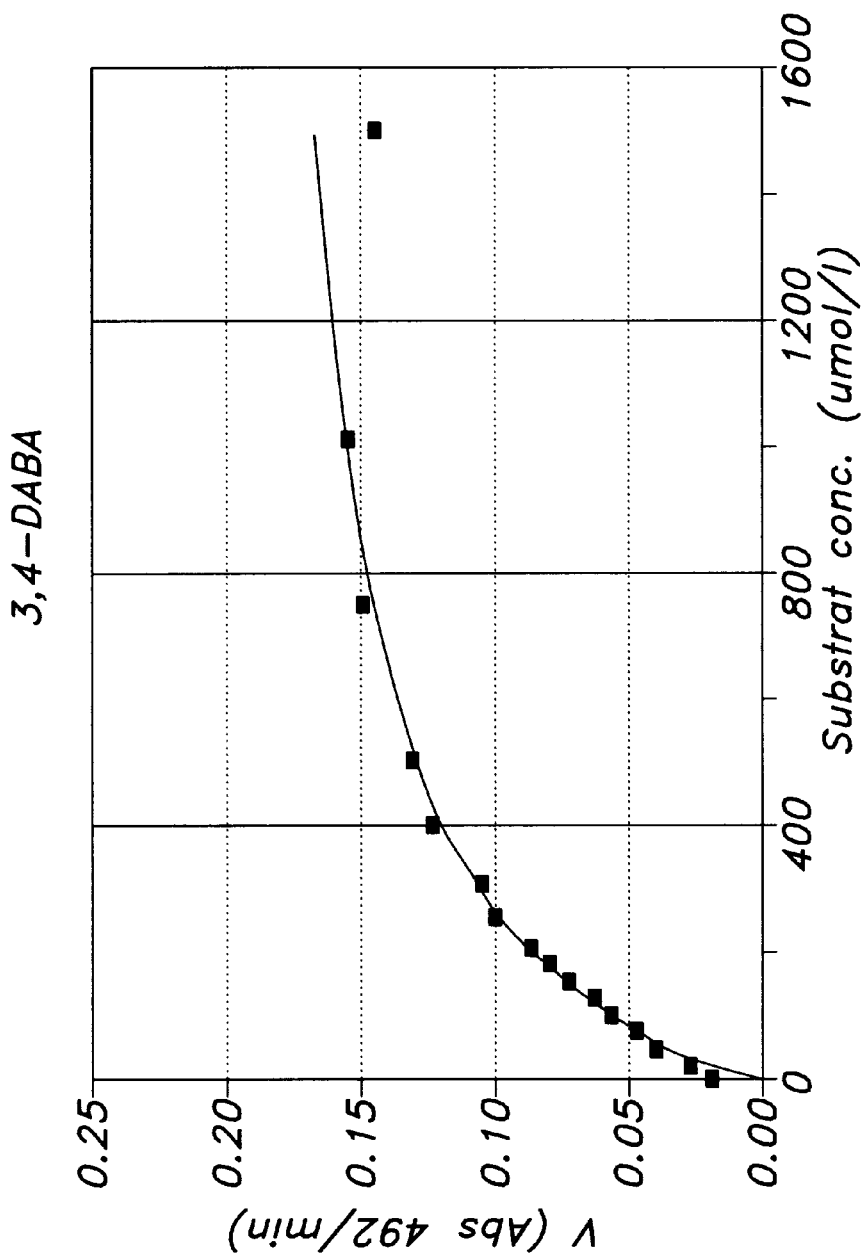
Figure 3:
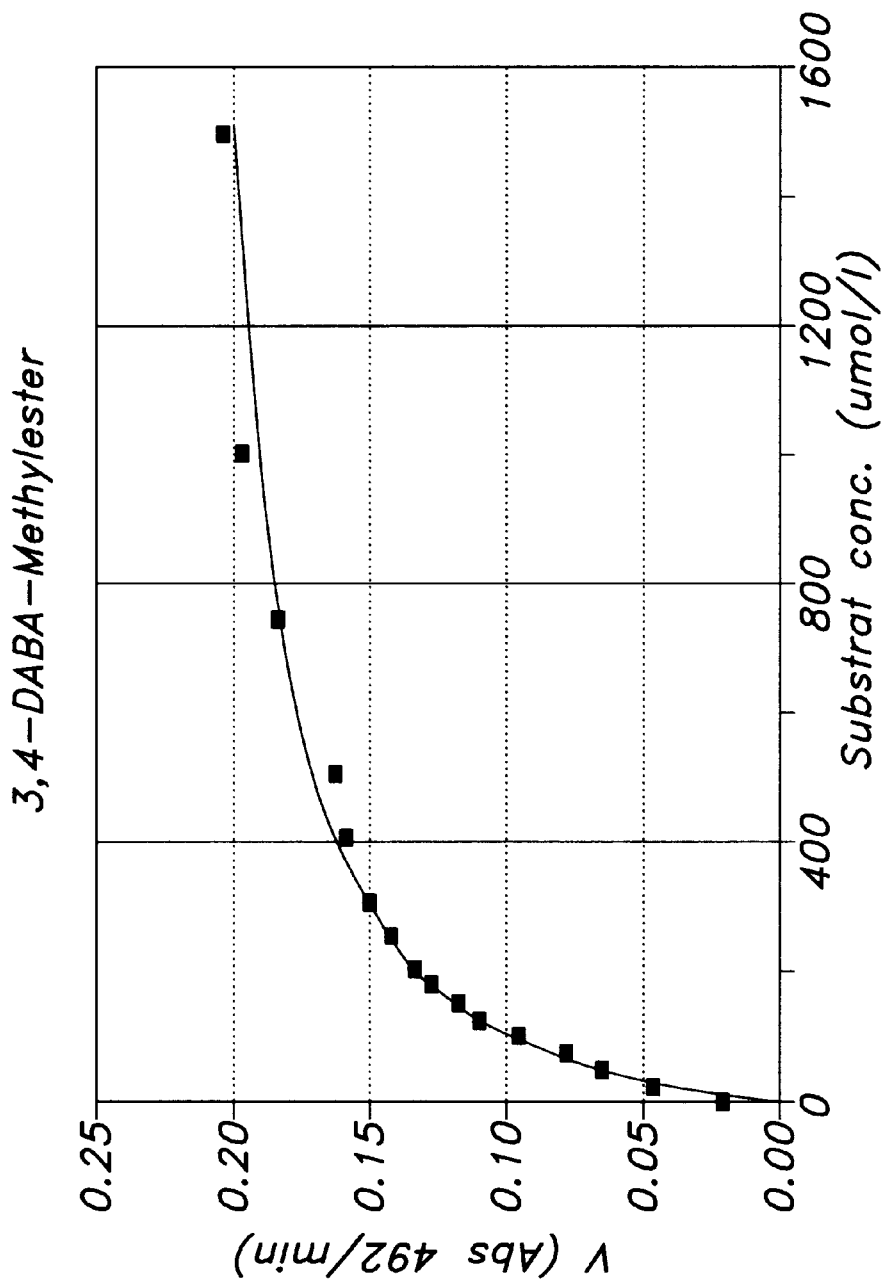
Figure 4:
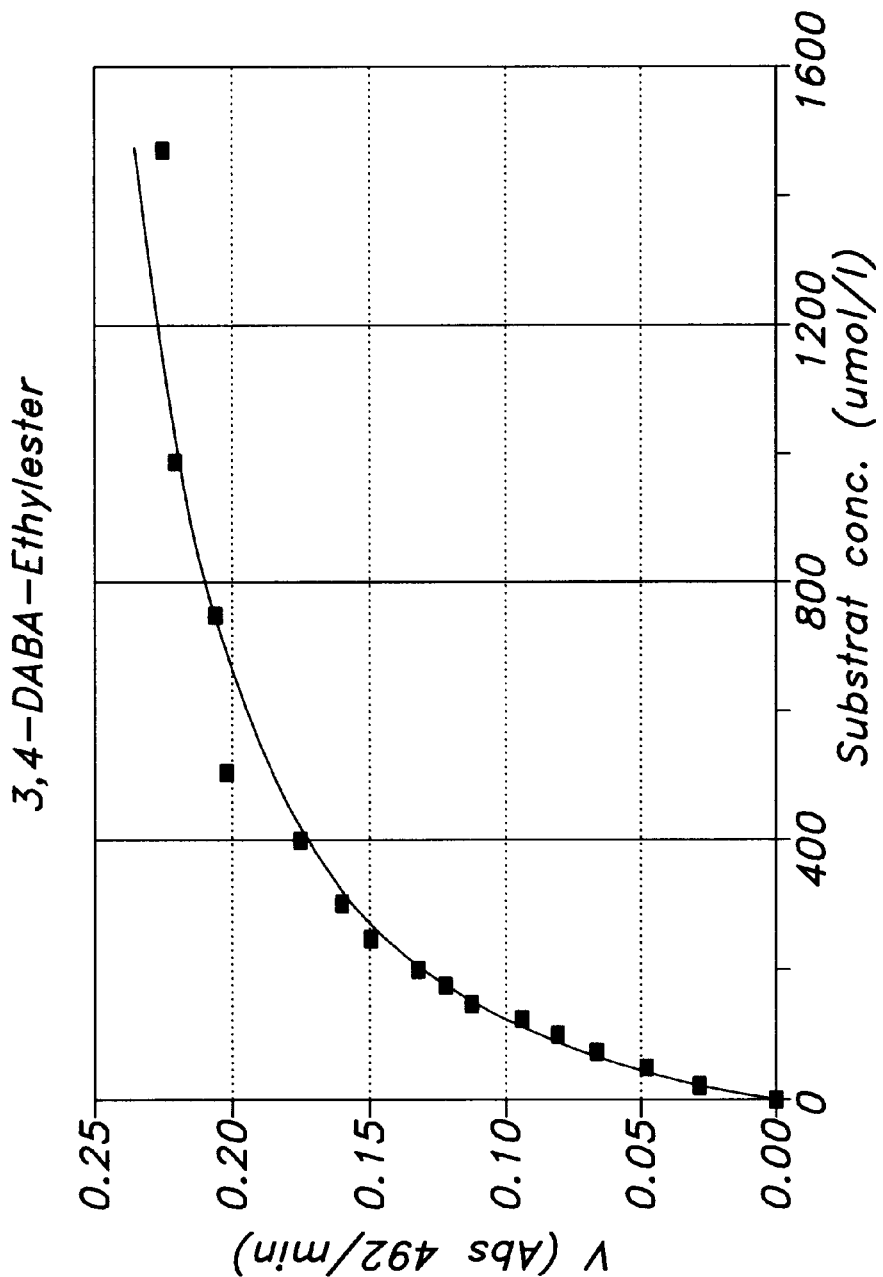
Figure 5:
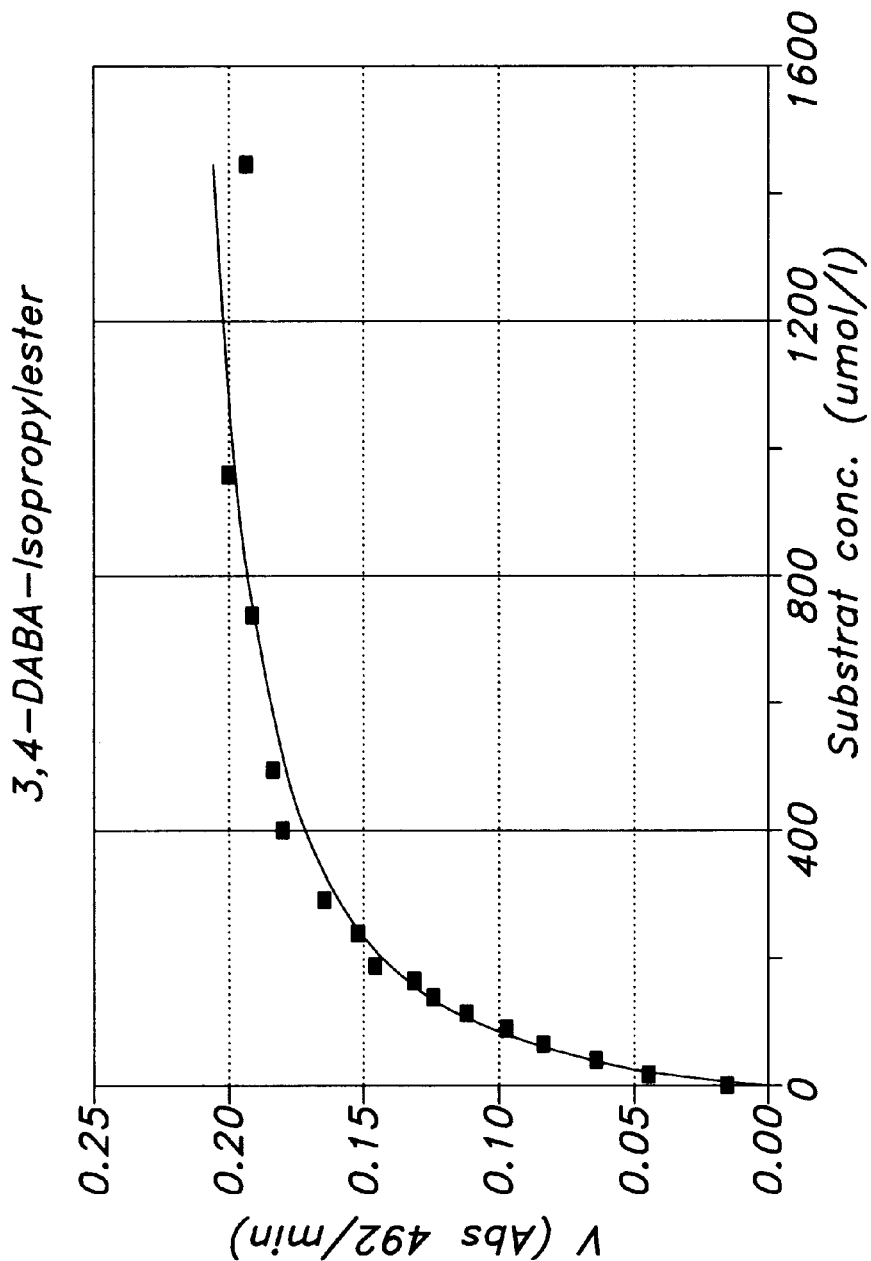

FIG. 1–5 is a graphic representation of the result of the measurement of initial velocity on OPD, 3,4-DABA, 3,4-DABA-methyl ester, 3,4-DABA-ethyl ester, 3,4-DABA-isopropyl ester.

Figure 6:
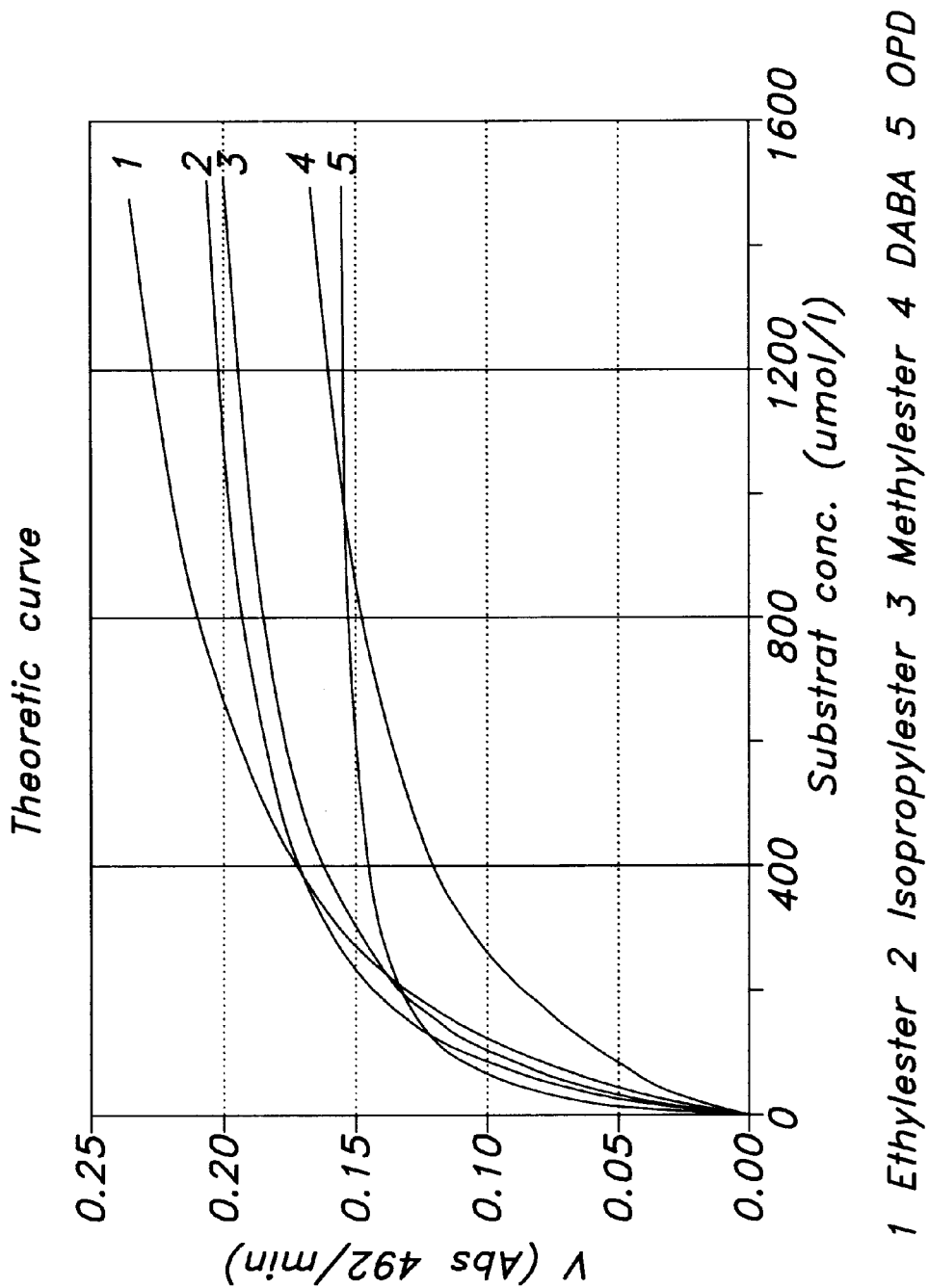

As is shown by Table 5 and FIGS. 1 to 6 the carboxyl esters of 3,4-DABA are effective substrates in a peroxidase/hydrogen peroxide system. It is possible to obtain much higher initial velocities with these compounds than with OPD. $K_m$ per se is a poor indicator of the effectiveness in enzyme assays of the substrates in question as it actually only shows the sensitivity of the system at low concentrations of substrate. In practice substrate concentrations would be chosen to allow maximum and linear colour development with different concentrations of enzymes. In other words $V_{max}$ and $K_{kat}$ are more relevant parameters for the comparison of different substrates. It was found that, for all the esters investigated, the values of $V_{max}$ and $K_{kat}$ were considerably larger than the comparable values for OPD.

All reaction velocities are expressed as absorption units, this is partly because most practical enzyme essays are based on the measurement of absorption and partly because the products of reaction are not isolated from the reaction mixture.

EXAMPLE 3
Determination of the Mutagenicity of the Compounds

The Ames test (Maron and Ames (1983)) was used to determine the mutagenic properties of the compounds. Nutrient media were prepared in the manner described by Venitt and Parry (1984). To 3×2 ml melted agar at 45° C. were added 100 μl of 50, 100 and 200 mM of solutions of the compounds dissolved in DMSO. By means of a pipette 100 μl of a well-grown culture of Salmonella tphiinuriium TA 98 (BIO-TEST gl. skolevej 47, 6731 Tiæreborg) were added to the same test-tube. The bacteria contain a frame-shift mutation on the histinol-dehydrogenase gene and require histidin in order to grow. Mutagenic aromatic amines can cause the bacteria to mutate to His+ and they can then grow on the nutrient medium. The number of colonies after incubation therefore give a quantitative measure of the ability of the added compound to cause mutation. In all trials spontaneous mutations take place in the absence of a mutagen. These provide a measure of "background" mutation.

Figure 7:
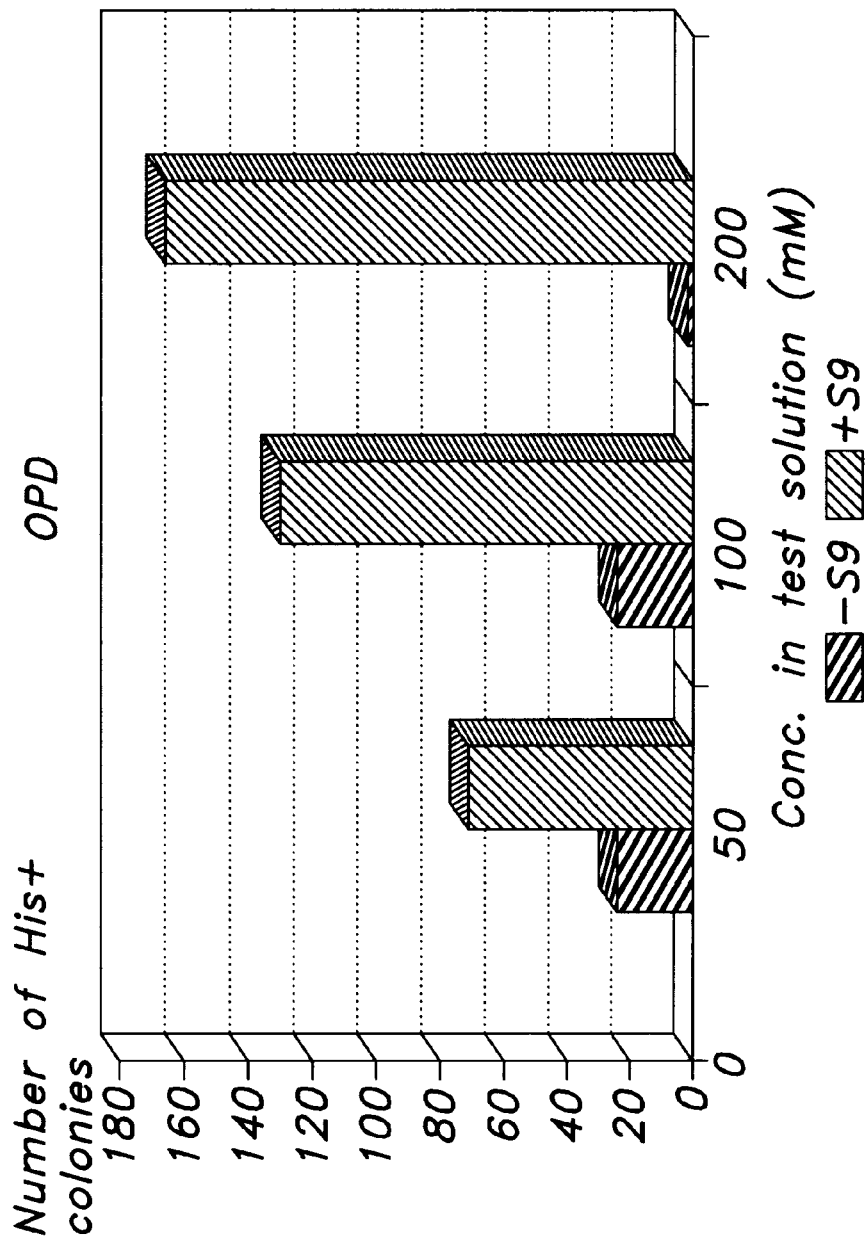
Figure 8:
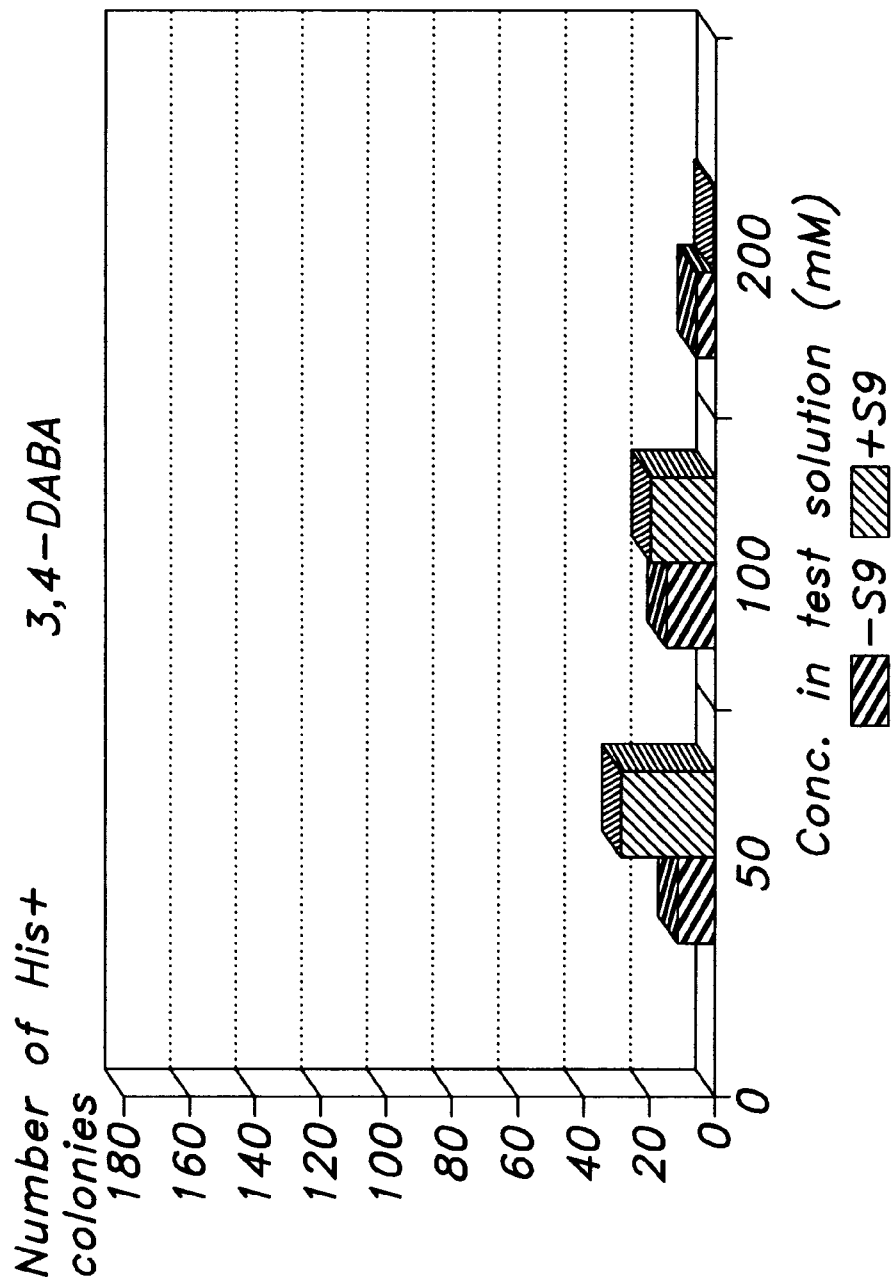
Figure 9:
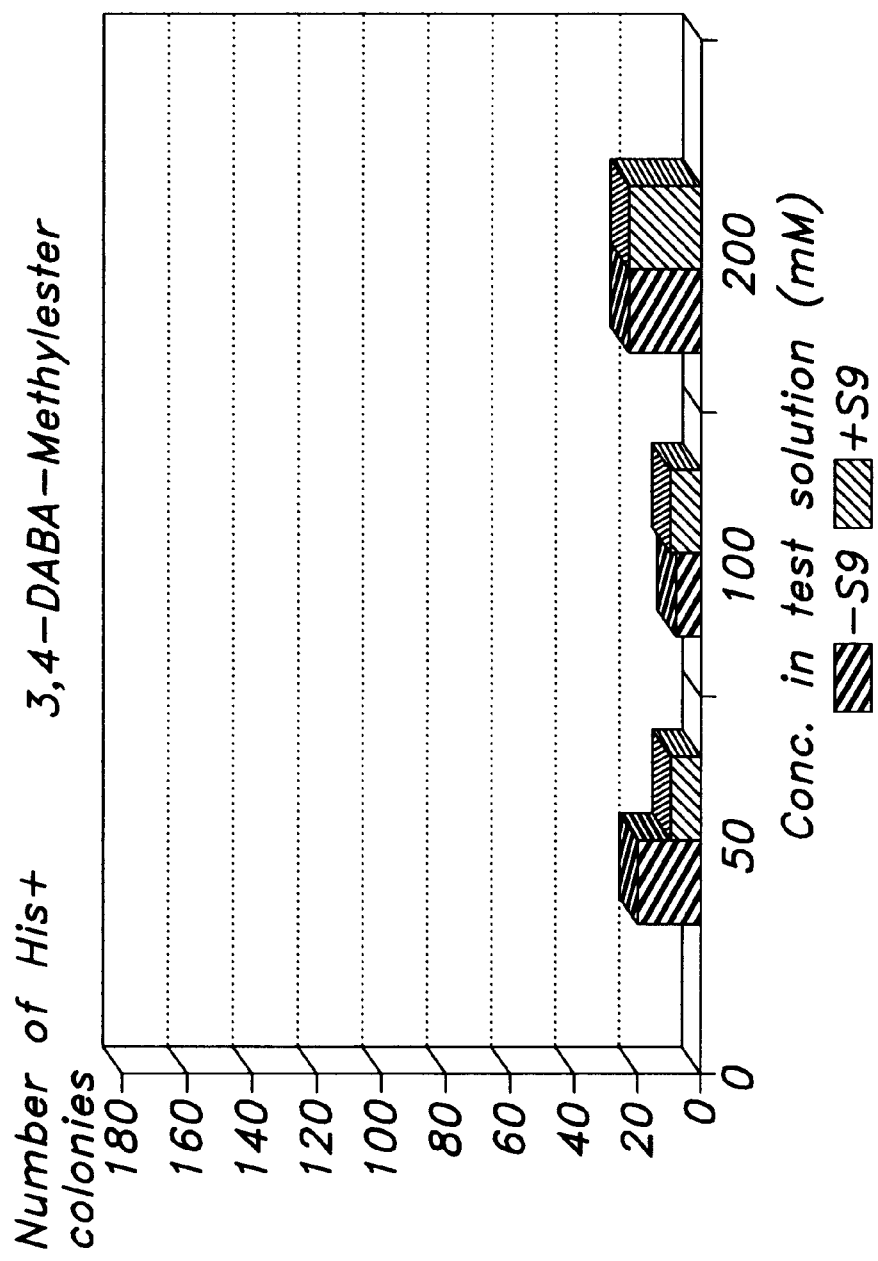
Figure 10:
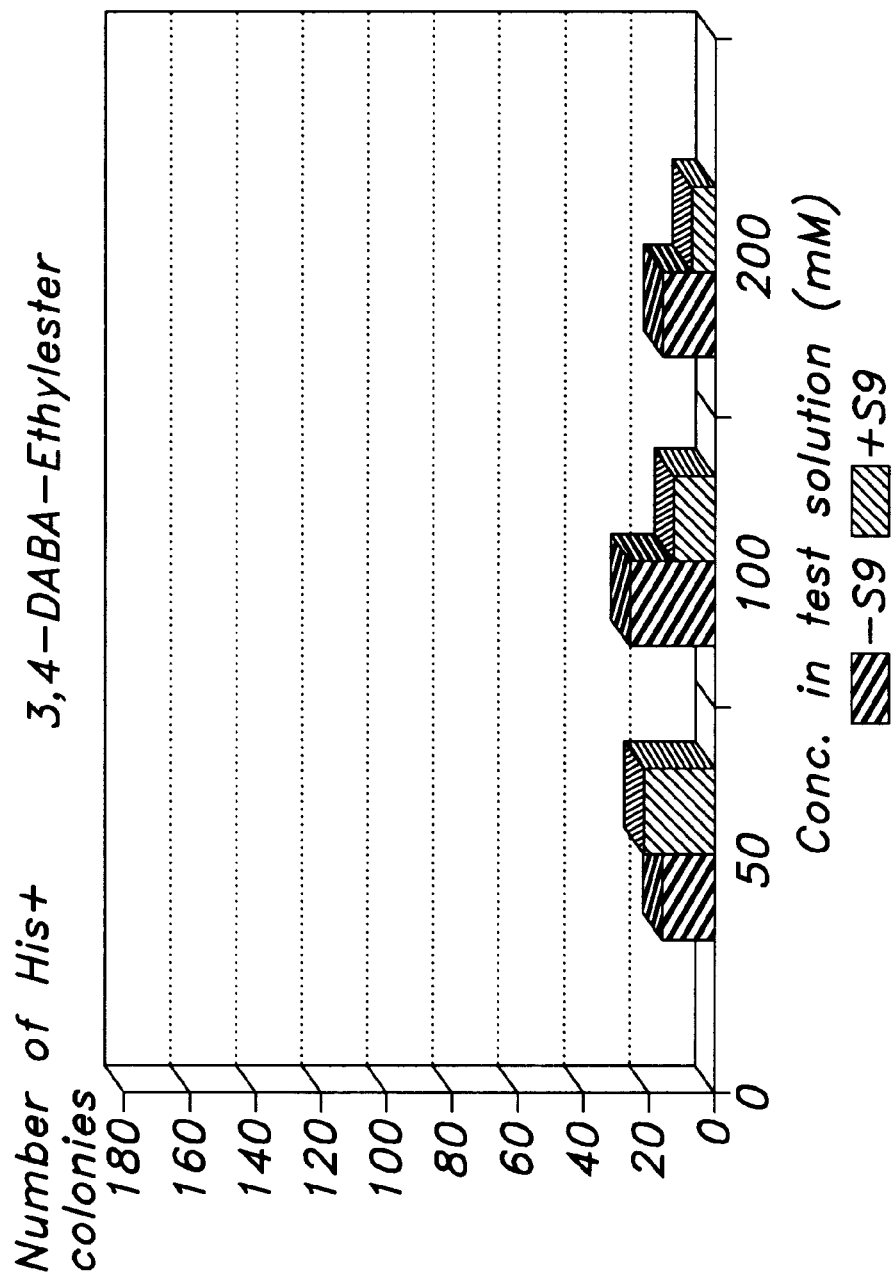
Figure 11:
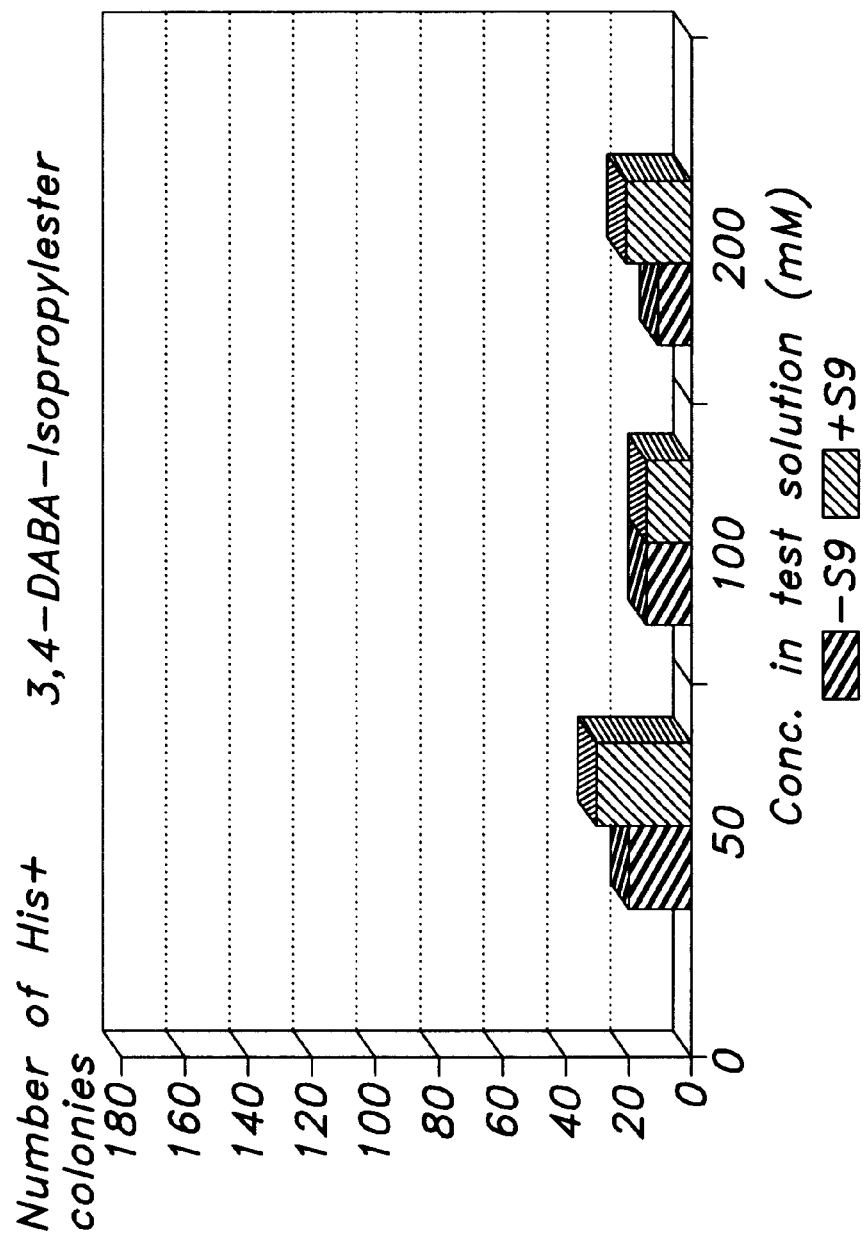

OPD is not a direct mutagen, it must first be activated by the liver enzyme system P450. All trials were therefore carried out both with and without the addition of "59-mix" from the livers of rats, this contains the P450 system. 0.5 ml of "59-mix" was added to each test-tube. The criteria for mutation are that increasing concentrations of the compound under investigation give a marked increase in the number of His+ mutants. The results of these trial are given in FIG. 7–11. It may be seen from this figure that only OPD has mutagenic properties.

EXAMPLE 4
Dyeing Effect of Dye Precursors of the Invention

The permanent oxidative dyeing effect of different dye precursors using 0.05 mg active enzyme protein *Myceliophthora thermophila* laccase (available from Novo Nordisk and described in WO 95/33836) per ml reaction mixture were tested.

The dye precursors tested were:

0.1% w/w 3,4 diamino benzoic acid (DABA) in 0.1M K-phosphatebuffer, pH 7.0.

0.1% w/w 3,4-diaminobenzoic acid methyl ester (DABA-Me) in 0.1 M K-phosphatebuffer, pH 7.0.

Modifier used:

0.1% w/w m-phenylenediamine (MPD) in 0.1 M K-phosphatebuffer, pH 7.0.

Dye precursor solutions were prepared by mixing the indicated modifier so that the final concentration in the dyeing solution was 0.1% w/w with respect to dye precursor (i.e. substrate of the invention) and 0.1% w/w with respect to modifier.

Hair Dyeing 1 gram 6" De Meo Virgin natural white hair tresses (De Meo Brothers Inc. USA) were used.

4 ml dye precursor solution (including modifier) was mixed with 1 ml laccase on a Whirley mixer, applied to the hair tresses and incubated at 30° C. for 30 minutes.

The hair tresses were then rinsed with running water, washed with shampoo, rinsed with water, combed, and air dried.

a*, b* and L* were determined on the Chroma Meter and ΔE* was then calculated as described below.

Hair tress samples treated without enzyme were used as a blind.

The result of the test is shown in Table 6.

TABLE 6

| 0.1% w/w dye precursor/modifier | DABA and DABA-Me with/without MPD | | | | |
|---|---|---|---|---|---|
| | ΔL | Δa | Δb | ΔE | Assessment |
| DABA | −4.27 | −0.63 | −2.55 | 5.01 | no colour |
| DABA + MPD | −23 | −2.21 | −18.29 | 29.47 | grayish |
| DABA-Me | −7.58 | 6.53 | −2.14 | 10.23 | light orange |
| DABA-Me + MPD | −32.31 | 2.35 | −25.07 | 40.96 | grayish violet |

Assessment of the Hair Colour

The quantitative colour of the hair tresses was determined on a Minolta CR200 Chroma Meter by the use the parameters L* ("0"=black and "100"=white), a* ("−"=green and "+"=red) and b* ("−" blue and "+" yellow).

ΔL*, Δa* and Δb* are the delta values of L*, a* and b* respectively compared to L*, a* and b* of untreated hair (e.g. $\Delta L^* = L^*_{sample} - L^*_{uncreated\ hair}$).

ΔE* was calculated as ΔE*=square root $(\Delta L^{*2} + \Delta a^{*2} + \Delta b^{*2})$ and is an expression for the total quantitative colour change.

EXAMPLE 5
Dyeing Effect of DAB-Me and Various Modifiers

Using the procedure described in Example 4 the permanent dyeing effect of the dye precursor (i.e. substrates) DABA-Me with various modifiers were tested, except that 0.2% w/w dye precursor and 0.2% modifier were used.

TABLE 2

| 0.2% DABA-Me and 0.2% w/w modifier | ΔL* | Δa* | Δb* | ΔE* | Assessment |
|---|---|---|---|---|---|
| 4-chlor-resorcinol | −22.36 | 1.19 | −6.28 | 23.26 | Gray-green |
| 5-amino-o-cresol | −14.1 | 5.69 | −2.1 | 15.35 | light orange |
| m-phenylene-diamine | −33.25 | 2.17 | −23.71 | 40.9 | Grey (Bluish) |
| pyrogallol | −29.47 | 5.74 | −7.69 | 30.99 | Brown |
| 4-methoxy-1,3-phenyl-enediamine | −39.24 | 2.33 | −19.73 | 43.98 | Brown-gray/black |

As can be seen the keratinous fibers can be dyed using DABA-Me and a modifier.

What is claimed is:

1. A method for dyeing human hair, said method comprising contacting the hair with a composition comprising:

1) at least one oxidation enzyme,
2) at least one compound of formula 1

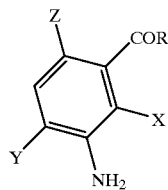 (I)

wherein
R is an amino, mono- or a disubstituted amino or OR', where R' is H, alkyl, alkenyl, alkynyl, halogenalkyl, nitro, benzyl, phenyl or substituted phenyl, X, Y and Z may each independently be hydrogen, alkyl, alkenyl, alkynyl, halogenalkyl, nitro, benzyl, phenyl, substituted phenyl, amino, hydroxy or mercapto with the proviso that at least one of the groups X, Y and Z is an amino group or a salt thereof, and
optionally 3) at least one modifier, for a period of time and under conditions sufficient to permit oxidation of the compound of formula (1) to a colored compound.

2. The method of claim 1, wherein the contacting is carried out at a pH in the range from 3.0 to 9.0.

3. The method of claim 2, wherein the pH is in the range of from 4.0 to 8.5.

4. The method of claim 2, wherein the pH is in the range of from 6.0 to 8.0.

5. The method of claim 1, wherein R' is a methyl, ethyl, or isopropyl group.

6. The method of claim 1, wherein the oxidation enzyme is an oxidoreductase selected from laccases, oxidases or peroxidases.

7. The method of claim 6, wherein the oxidation enzyme is a laecase derived from a strain selected from the group consisting of Polyporus sp., Myceliophthora sp., Rhizocionia sp., Rhus sp., Scytalidium and Pyricularia sp.

8. The method of claim 7, wherein the strain of Polyporus sp. is *P. pinsitus* or *P. versicolor*, the strain of Myceliophihora is *M. thermophila*, the strain of Rhizoctonia is *Rh. praticola* or *Rh. solani*, the strain of Rhus is *Rhus vernicifera*, the strain of Scytalidium is *S. thermophilium*, and the strain of Pyricularia is *P. oryzae*.

* * * * *